US008962235B2

(12) United States Patent
MacDonald et al.

(10) Patent No.: US 8,962,235 B2
(45) Date of Patent: Feb. 24, 2015

(54) CAPILLARY TRANSPORT

(75) Inventors: Michael MacDonald, Fife (GB);
Kishan Dholakia, Fife (GB); Igor Andreev, Fife (GB)

(73) Assignee: The University Court of the University of St. Andrews, St. Andrews (GB)

( * ) Notice: Subject to any disclaimer, the term of this patent is extended or adjusted under 35 U.S.C. 154(b) by 909 days.

(21) Appl. No.: 12/442,327

(22) PCT Filed: Sep. 20, 2007

(86) PCT No.: PCT/GB2007/003573
§ 371 (c)(1),
(2), (4) Date: Jun. 23, 2009

(87) PCT Pub. No.: WO2008/035080
PCT Pub. Date: Mar. 27, 2008

(65) Prior Publication Data
US 2010/0047761 A1 Feb. 25, 2010

(30) Foreign Application Priority Data

Sep. 21, 2006 (GB) .................................. 0618605.0
Jan. 15, 2007 (GB) .................................. 0700737.0

(51) Int. Cl.
C12N 5/078 (2010.01)
C12M 1/00 (2006.01)
G01N 15/14 (2006.01)
(52) U.S. Cl.
CPC .......... *C12M 47/04* (2013.01); *G01N 15/1484* (2013.01); *G01N 2015/149* (2013.01)
USPC ...... 435/2; 435/173.6; 435/173.7; 435/173.9; 435/261; 435/325; 435/372; 210/748.06; 210/748.09; 210/748.1; 210/768; 209/155
(58) Field of Classification Search
None
See application file for complete search history.

(56) References Cited

U.S. PATENT DOCUMENTS

| 3,710,279 | A | | 1/1973 | Ashkin | |
|---|---|---|---|---|---|
| 4,523,682 | A | | 6/1985 | Barmatz et al. | |
| 5,158,889 | A | * | 10/1992 | Hirako et al. | ............... 435/286.3 |
| 5,245,466 | A | | 9/1993 | Burns et al. | |
| 5,938,904 | A | | 8/1999 | Bader et al. | |
| 6,216,538 | B1 | | 4/2001 | Yasuda et al. | |
| 6,416,190 | B1 | | 7/2002 | Grier et al. | |
| 6,548,124 | B1 | | 4/2003 | Brumer et al. | |
| 6,833,542 | B2 | | 12/2004 | Wang et al. | |
| 6,974,927 | B2 | | 12/2005 | Hannah | |
| 7,161,140 | B2 | | 1/2007 | Grier et al. | |
| 7,351,953 | B2 | | 4/2008 | Grier et al. | |
| 7,449,679 | B2 | | 11/2008 | Plewa et al. | |
| 8,816,234 | B2 | | 8/2014 | MacDonald et al. | |
| 2002/0160470 | A1 | | 10/2002 | Zhang | |
| 2002/0185592 | A1 | | 12/2002 | Grier et al. | |
| 2003/0007894 | A1 | | 1/2003 | Wang et al. | |
| 2003/0047676 | A1 | | 3/2003 | Grier et al. | |
| 2003/0111594 | A1 | | 6/2003 | Getin | |
| 2004/0021949 | A1 | * | 2/2004 | Grier et al. | ..................... 359/614 |
| 2004/0067167 | A1 | | 4/2004 | Zhang et al. | |
| 2004/0089798 | A1 | * | 5/2004 | Gruber et al. | ................. 250/251 |
| 2005/0247866 | A1 | | 11/2005 | Plewa | |
| 2006/0177940 | A1 | | 8/2006 | Furst | |
| 2010/0047761 | A1 | | 2/2010 | MacDonald et al. | |

FOREIGN PATENT DOCUMENTS

| CA | 2493411 | 2/2004 |
|---|---|---|
| DE | 19952322 | 5/2001 |
| JP | 05 026799 | 2/1993 |
| WO | WO 98/10267 | 3/1998 |
| WO | WO 02/084276 | 10/2002 |
| WO | WO 03/062867 | 7/2003 |
| WO | WO 02/087792 | 11/2003 |
| WO | WO 2004/012133 | 2/2004 |
| WO | WO 2004/082840 | 9/2004 |
| WO | WO 2004/100175 | 11/2004 |
| WO | WO 2005/054818 | 6/2005 |
| WO | WO 2005/054832 | 6/2005 |
| WO | WO 2006/004558 | 1/2006 |
| WO | WO 2006/032844 | 3/2006 |
| WO | WO 2006/059084 | 6/2006 |

OTHER PUBLICATIONS

Dharmadhikari, Ja et al. Torque-generating malaria-infected red blood cells in an optical trap. Optics Express. 2004. 12(6): 1179-1184.*
Padgett, et al.; "The Angular Momentum of Light: Optical Spanners and the Rotational Frequency Shift," *Optical and Quantum Electronics*, pp. 1-12, vol. 31, No. 1, Chapman and Hall, London, Great Britain, 1999.
Padgett, et al.; "Optical Tweezers and Spanners," *Physics World*, Sep. 1997, pp. 35-38, IOP Publishing, Bristol Great Britain.
Ramser, et al.; "A Microfluidic System Enabling Raman Measurements of the Oxygenation Cycle in Single Optically Trapped Red Blood Cells," *Lab on a Chip*, Feb. 21, 2005, pp. 431-436, No. 5, Royal Society of Chemistry, Cambridge, Great Britain.
International Search Reported dated Jul. 1, 2008, for application PCT/GB2007/003573, filed Sep. 20, 2007.
M.P. MacDonald, G.C. Spalding and K. Dholakia; *Microfluid Sorting in an Optical Lattice*; Nature, Nov. 27, 2003; pp. 421-424; vol. 426, 2003 Nature Publishing Group (XP-002289740).
Jennifer E. Curtis, Brian A. Koss and David G. Grier;*Dynamic Holographic Optical Tweezers*; Optics Communications; Jun. 15, 2002; pp. 169-175; vol. 207; 2002 Elsevier Science B.V.

(Continued)

*Primary Examiner* — Allison Fox
*Assistant Examiner* — Susan E Fernandez
(74) *Attorney, Agent, or Firm* — Alston & Bird LLP

(57) ABSTRACT

A method for sorting particles, in particular cells A and B. The method uses a single channel with only one input and only one output. A particle mix A and B in a fluid is introduced into the channel and particles within the channel are sorted.

15 Claims, 2 Drawing Sheets

(56) References Cited

OTHER PUBLICATIONS

Eric R. Dufresne and David G. Grier; *Optical Tweezer Arrays and Optical Substrates Created with Diffractive Optics*; Review of Scientific Instruments; May 5, 1998; pp. 1974-1977; vol. 69, No. 5; 1998 American Institute of Physics.

J. Han and H.G. Craighead; *Separation of Long DNA Molecules in a Microfabricated Entropic Trap Array*; Science; May 12, 2000; pp. 1026-1029; vol. 288.

Dmytro Nykypanchuk, Helmut H. Strey and David A. Hoagland; *Brownian Motion of DNA Confined Within a Two-Dimensional Array*; Science; Aug. 9, 2002; pp. 987-990; vol. 297.

Deniz Ertas; *Lateral Separation of Macromolecules and Polyelectrolytes in Microlithographic Arrays*; Physical Review Letters; Feb. 16, 1998; pp. 1548-1551; vol. 80, No. 7, 1998 The American Physical Society.

T.A.J. Duke and R.H. Austin; *Microfabricated Sieve for the Continuous Sorting of Macromolecules*; Physical Review Letters; Feb. 16, 1998; pp. 1552-1555; vol. 80, No. 7; 1998 The American Physical Society.

Chia-Fu Chou, Jonas O. Tegenfeldt, Olgica Bakajin, Shirley S. Chan, Edward C. Cox, Nicholas Darnton, Thomas Duke and Robert H. Austin; *Electrodeless Dielectrophoresis of Single- and Double-Stranded DNA*; Biophysical Journal; Oct. 2002; pp. 2170-2179; vol. 83; 2002 Biophysical Society.

Pamela T. Korda, Michael B. Taylor and David G. Grier; *Kinetically Locked-In Colloidal Transport in an Array of Optical Tweezers*; Physical Review Letters; Sep. 16, 2002; pp. 128301-1-128301-4; vol. 89, No. 12; 2002 The American Physical Society.

International Search Report for PCT/GB2004/001993 completed Jul. 23, 2004.

Office Action dated Apr. 27, 2009, Canadian Application No. 2,524,646.

Office Action dated Feb. 8, 2010, Canadian Application No. 2,524,646.

Office Action dated Nov. 5, 2008, U.S. Appl. No. 10/554,937.

Office Action dated May 5, 2009, U.S. Appl. No. 10/554,937.

Office Action dated Feb. 17, 2011, U.S. Appl. No. 10/554,937.

Office Action dated Jun. 16, 2011, U.S. Appl. No. 10/554,937.

Office Action dated Nov. 30, 2011, U.S. Appl. No. 10/554,937.

Office Action dated Sep. 13, 2012, U.S. Appl. No. 10/554,937.

Office Action dated Apr. 5, 2013, U.S. Appl. No. 10/554,937.

Sancho, et al., "Reply" *Physical Review Letters*, May 12, 2005, Article 188902, vol. 94, The American Physical Society.

Paterson, et al., "Light-induced Cell Separation in a Tailored Optical Landscape," *Applied Physics Letters*, Sep. 13, 2005, Article 123901, vol. 87.

International Search Reported dated Apr. 23, 2008, Application No. PCT/GB2007/003578, filed Sep. 20, 2007.

Office Action dated Aug. 23, 2011, U.S. Appl. No. 12/442,325.

Office Action dated Feb. 16, 2011, U.S. Appl. No. 12/442,325.

Office Action dated Jul. 24, 2012, U.S. Appl. No. 12/442,325.

Notice of Allowance dated Dec. 24, 2012, U.S. Appl. No. 12/442,325.

\* cited by examiner

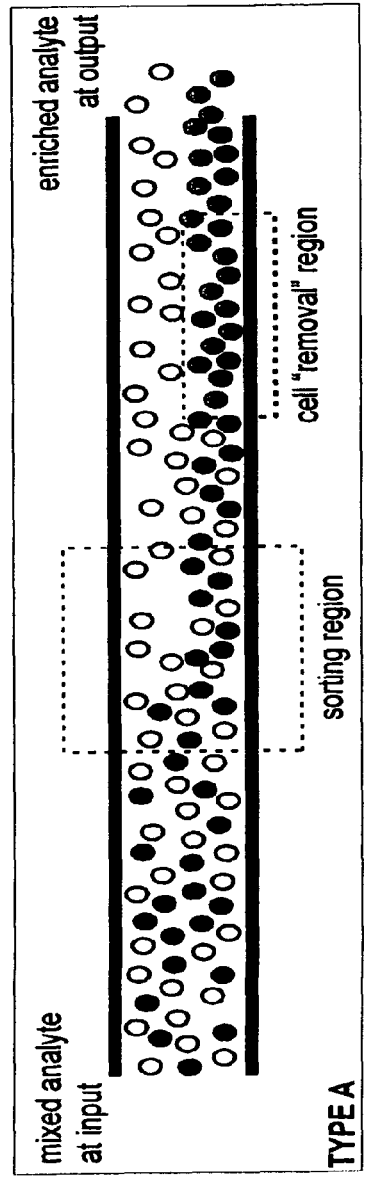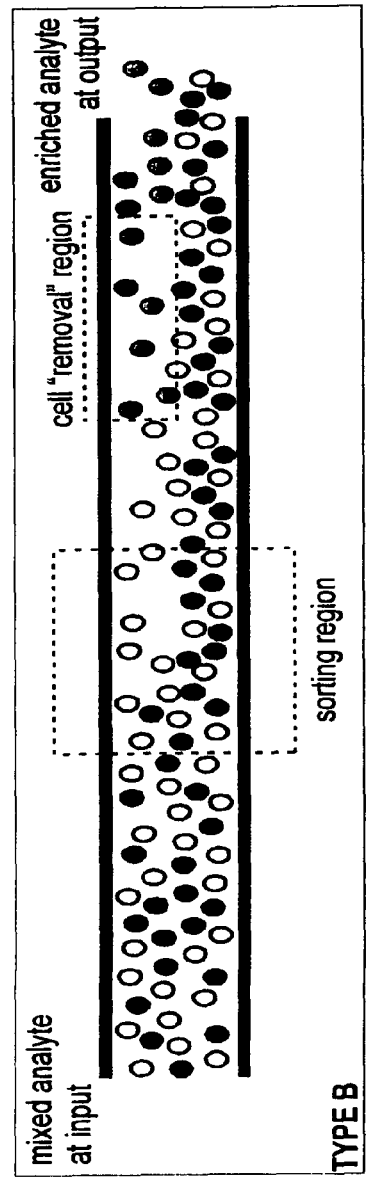
Figure 1
Figure 2

CAPILLARY TRANSPORT

The present invention relates to optical sorting of particles, and in particular cells.

BACKGROUND OF THE INVENTION

Many particle sorting or separation schemes exist, ranging from gel-electrophoresis, capillary electrophoresis, and analytical centrifuging to novel, entropic barriers. Examples of these are described by J. Han, H. G. Craighead, Science 288, 1026-1029 (May 12, 2000) and D. Nykypanchuk, H. H. Strey, D. A. Hoagland, Science 297, 987-990 (Aug. 9, 2002). The majority of these known techniques separate a polydisperse mixture in a flowing fluid into bands containing particles that travel at different velocities along the direction of flow. This typically leads to batch processing. In electrophoresis a gel is used to obtain a size-dependent mobility. Recovery of fractions is achieved through post-processing of the gel. However, despite its widespread use and effectiveness this methodology is slow and importantly, due to limited pore sizes, has difficulty in separating objects at the microscopic size level, for example cells, chromosomes and colloidal matter.

Lithographically fabricated two-dimensional, asymmetric artificial gels are also used. Examples of these are described by D. Ertas, Physical Review Letters 80, 1548-1551 (Feb. 16, 1998); T. A. I Duke, R. H. Austin, Physical Review Letters 80, 1552-1555 (Feb. 16, 1998) and C. F. Chou et al., Biophysical Journal 83, 2170-2179 (October 2002). These gels yield separation transverse to the direction of flow. Because of this, they can be operated in a continuous fashion, with various fractions taken up by separate collection channels. However, sorting based on diffusion is impractically slow at the microscopic scale.

In recent years there has been growth in the exploration of particle motion on optical landscapes. An example of this is described in the article "Kinetically Locked-in Colloidal Transport in an Array of Optical Tweezers" by P. T. Korda et al, Physical Review Letters 89, Number 12, Art. No. 128301 (16 Sep. 2002). In this case, a monolayer of colloidal spheres is allowed to flow through an array of discrete optical traps. By varying the orientation of the array of traps, the direction of flow of the spheres can be varied. Because of this, it has been suggested that the lattice could be used to continuously fractionate mesoscopic particles. However, because of the use of a lattice of localized discrete traps, the observed kinetically locked-in channelling along low-index lattice vectors is intrinsically limited to small-angle deflections. In practice, this limits the practicality of the lattice for use in fractionation.

PCT/GB2004/001993 describes yet another optical fractionation scheme. In this, three-dimensional optical lattices are used for sorting and fractionation of biological and colloidal material in a microfluidic flow. Different particles follow different trajectories across the landscape and consequently exit at different points. The selectivity and basis of this form of sorting is the affinity of a given particles to the features of the optical landscape. This is also described by M. MacDonald, G. Spalding and K. Dholakia, in Nature 426, 421 (2003), and by A. M. Lacasta, et al., in Physical Review Letters (2005), 94, 188902. Even in the absence of fluid flow periodic optical patterns may be used for sorting, see L. Paterson, et al., Applied Physics Letters (2005), 87, 123901.

One of the main advantages of using optically defined microfluidic sorting is that the requirements on the physical microfluidics can be kept to a minimum. Nevertheless, in some circumstances there is a need for an even simpler arrangement.

SUMMARY OF THE INVENTION

According to the present invention, there is provided a sorting method that uses a single microfluidic channel or other suitable conduit such as a microcapillary having an elongate channel with only one exit in the fluid flow direction, the method involving introducing a particle mix in a fluid into the channel, and optically sorting particles within the channel. Once the particles are sorted, they can then be treated further whilst still within the channel.

By providing a very simple channel arrangement and optically sorting particles within that channel, no physical separation of sorted particles into separate channels is required.

Sorting the particles may involve physically separating them into different regions of the channel or subjecting the particles to an optical potential that only one type is sensitive to. In the latter case, the particle mix may be subjected to an optical potential that preferentially damages or de-activates one type of particle, so that the output is a sample that is enriched with one or more other types of particle. Where cells are being sorted, the optical potential may be chosen to preferentially kill or damage one type of cell. For example the method may be for sorting white and red cells and may involve using an optical field to cause the red cells to flip, that is rotate by 90 degrees and align with the light field, thereby causing physical damage to those cells, for example to the cell membrane. The optical field may comprise an optical funnel. One or more lines of light may be used to define the optical funnel.

The method may involve processing, for example treating and/or sampling and/or measuring a characteristic of, the sorted particles whilst still within the channel. The sorted particles that are processed may be all of one type or may be a mix of particle types.

In one embodiment, a laser is used to kill cells in part of the flow after sorting, so that only the desired cells leave the channel alive or active. In this way, a single channel can be used with only one input and one output.

Alternatively, instead of killing unwanted cells, selected cells can undergo a second optical process whilst still within the sorting channel. The second optical process could be for example optoporation as described in WO2006/059084, the contents of which are incorporated herein by reference.

Additionally or alternatively, the second optical process may be some form of spectroscopy, such as raman spectroscopy, as described in our co-pending patent application GB 0611289.0, the contents of which are incorporated herein by reference.

The optical sorting may be done using an optical landscape or pattern that is defined by an acousto-optic device, as described in our co-pending patent application GB 0618606.8, the contents of which are incorporated herein by reference.

According to another aspect of the invention, there is provided a system for sorting particles, in particular cells, comprising a single channel with only one output and means for sorting particles within that channel.

Preferably, the single channel has a single input and the particle mix is introduced via that input.

The channel may be a microfluidic channel and particles are preferably introduced in a fluid flow. Preferably the channel is a micro-capillary.

Preferably, the means for sorting comprise means for sorting the particles optically. The means for optically sorting the particles may comprise an acousto-optic device.

Means may be provided for treating and/or sampling and/or measuring a characteristic of the sorted particles, whilst still within the channel. The means for treating may comprise means for killing or de-activating particles in at least part of the channel and/or means for porating particles in at least a part of the channel. The means for measuring may comprise means for measuring a spectra, for example a raman spectra.

BRIEF DESCRIPTION OF THE DRAWINGS

Various aspects of the invention will now be described by way of example only and with reference to the accompanying drawings, of which:

FIG. 1 is cross-section through a micro-fluidic channel with a cell sorting region and a cell removal region;

FIG. 2 shows a variation on the arrangement of FIG. 1, and

SPECIFIC DESCRIPTION OF THE DRAWINGS

Figure 3:
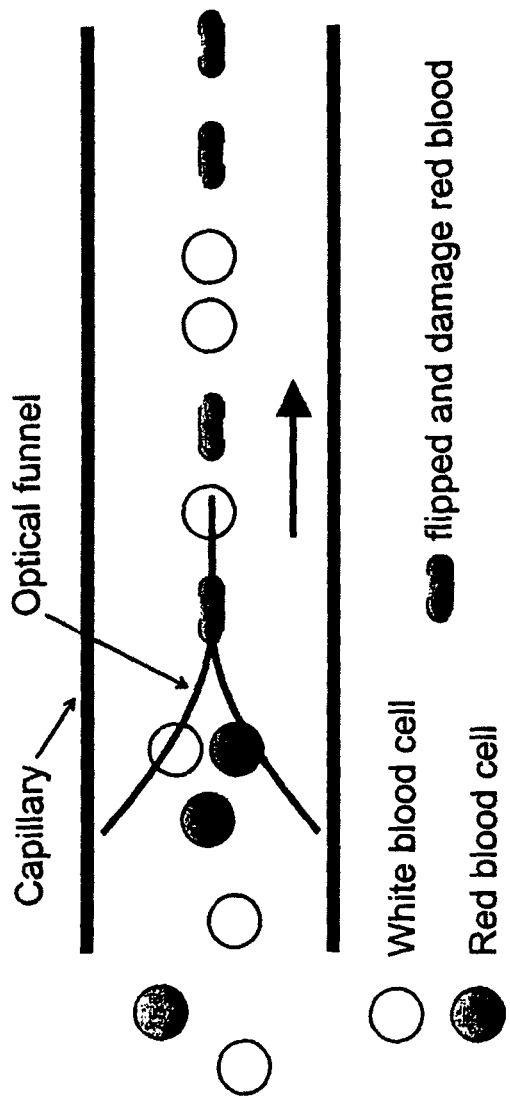
FIG. 3 shows an alternative micro-fluidic cell sorting arrangement.

FIGS. 1 and 2 show a single microfluidic channel for sorting, for example cells. The channel is cylindrical with a constant cross section, its ends defining an input and an output. The channel has a sorting region in series with a cell-processing region, for example an optical cell removal region. An analyte of interest is injected into one end of the micro-channel, flows through the channel and into the sorting region, where sorting is done using any suitable means, preferably optical means. Techniques for doing this are know in the art and so will not be described in detail. The optical sorting is done using an optical arrangement that is effective in a localised region of the channel, and not along its full length.

Once the cells are sorted, they move downstream in the fluid flow to the cell removal region. This region extends only partially over the flow path, so that some cells enter it, but others do not. Within this region cells are removed by a laser that makes them either non-viable or destroys them. To achieve this, a portion, typically half, of the channel, as measured across its width, is illuminated with a laser at a wavelength and average power/peak power that will kill or damage any cell. The material that is then taken from the other end of the conduit contains an enriched flow of cells, as only the cells that have not passed through the removal region are viable.

FIG. 1 shows how a pure flow of cells can be created from a mix of cells A and B, but with the loss of about half of the desired cell species. In this case, the cell removal region extends over a lower portion of the channel and the optical potential/landscape in the optical sorting region of is arranged so that the B cells are deflected towards the lower part of the channel, but the A cells are substantially unaffected and remain distributed throughout the channel. When the particle mix flows into the cell removal region, the A cells are present in the upper channel region, but a mixture of the A and B cells is present in the lower region of the channel. Since the cell removal region extends partially over the lower part of the channel, the A cells in the upper region pass through unaffected, whereas cells in the A and B mix are damaged or killed or made otherwise biologically inactive. Therefore, at the channel output only A cells are active, thereby providing an enriched analyte.

FIG. 2 shows a variation on FIG. 1, in which a sample mix of A and B cells can be sorted and processed to provide an enrichment of approximately 50%, whilst at the same time ensuring that no cells of the desired species are destroyed. In this case, the cell removal region extends over the upper part of the channel. As before, the optical potential/landscape in the optical sorting region is arranged so that the B cells are deflected towards the bottom of the channel as the fluid flows through the cell-sorting region, but the A cells are substantially unaffected and remain distributed throughout the channel. Hence, when the A and B cell mix flows into the cell removal region, A cells are present in the upper channel region, but a mixture of A and B cells is present in the lower region of the channel. In this case, because the cell removal region extends partially over the upper region of the channel, only A cells are exposed to the removal radiation. Hence, as the A and B call mix flows through the removal region the A cells in the upper region are rendered biologically inactive, whereas cells in the A and B mix in the lower region are unaffected.

Whilst the arrangement of FIG. 2 results in a mix of live cells at the output, this mix will have more B cells than A cells. Re-circulating the fluid will lead to higher levels of enrichment. This could be achieved simply by switching of the sorting and cell removal regions, reversing the flow and re-starting process. This approach might be attractive when trying to sort out cell species with a very low population compared to other cell types in the analyte.

Whether the arrangements of FIG. 1 or FIG. 2 are used depends upon the ratio of cell species entering the channel, the level of enrichment required by the user, and whether or not it is acceptable to lose 50% of the desired cells.

As an alternative to causing damage, sorted cells could be processed. For example, in the example of FIG. 1 the A cells in the upper part of the channel could be targeted by a second laser and porated, such that either a chemo or gene agent within the medium can be transfected into them. As an example, transfection could be used to test for antibiotic resistance or for express of green fluorescent protein. In a preferred embodiment the porating laser output is in the form of a Bessel beam but may also be achieved with a gaussian beam. As described in WO2006/059084, this can provide significant technical advantages. Hence, in the output there will be a select population of cells that have been treated. Another option is to obtain Raman data from the sorted cells. This can be done using the techniques described in our co-pending patent application GB 0611289.0, the contents of which are incorporated herein by reference.

FIG. 3 shows another optical landscape for sorting cells in a micro-capillary. The optical landscape works by subjecting the cells to an optical field that only one type is sensitive to. In this case, the landscape is an optical funnel that focuses down a broad flow of particles into a single or dual file flow of particles. The cell mix is subjected to an optical field that damages or otherwise de-activates one type of cell, so that it ceases or is unable to fulfill its biological function. The result is that the output is a sample that is enriched with one or more other types of cell.

Advantageously, the arrangement of FIG. 3 can be used for sorting red cells from white cells. Red cells are bi-concave discs and white cells are generally spherical. The optical landscape used to sort these is in two dimensions and typically is funnel shaped, with the funnel narrowing in the direction of fluid flow. A fluid containing a mixture of red and white cells is introduced into the micro-capillary and caused to flow towards the narrow end of the funnel. The flow of white cells is focussed down by the funnel but otherwise passes through unaffected. In contrast, the red cells flip to align with the narrow output of the optical funnel and become damaged or lysed due mechanical stresses induced in the violent flipping process, so that only active white cells make it through. In this way, the output is enriched with white cells.

A skilled person will appreciate that variations of the disclosed arrangements are possible without departing from the invention. Accordingly the above description of the specific embodiment is made by way of example only and not for the purposes of limitation. It will be clear to the skilled person that minor modifications may be made without significant changes to the operation described.

The invention claimed is:

1. A method for sorting cells comprising:
providing a single channel with only one output;
introducing a mix of cell types in a fluid flow into the channel;
in a sorting region in the channel, optically deflecting one of the cell types to cause the deflected cells to flow into or away from a removal region that extends only partially over the fluid flow path and the removal region is downstream from the channel sorting region; and
killing or de-activating cells that flow into the removal region, thereby to provide an enriched sample at the channel output,
wherein at least some cells do not flow into the removal region and flow to the channel output.

2. A method as claimed in claim 1 wherein the single channel has a single input and the cell mix is introduced via that input.

3. A method as claimed in claim 1 wherein the channel is a microfluidic channel.

4. A method as claimed in claim 1 comprising treating and/or sampling and/or measuring a characteristic of the sorted cells whilst still within the channel.

5. A method as claimed in claim 4 comprising killing or de-activating cells in at least part of the channel.

6. A method as claimed in claim 4 comprising porating cells in at least a part of the channel.

7. A method as claimed in claim 6 comprising introducing material into the porated cells.

8. A method as claimed in claim 4 comprising making a spectroscopic measurement of the sorted sample.

9. A method as claimed in claim 8 wherein the spectroscopic measurement is a Raman spectra.

10. A method as claimed in claim 4 wherein treating and/or sampling and/or measuring of the sorted cells is done in a region that extends partially across the channel.

11. A method as claimed in claim 1 wherein the single channel is a micro-capillary.

12. A method as claimed in claim 1 further comprising the step of using an optical field to cause at least some of the cells to flip.

13. A method as claimed in claim 12 wherein the optical field comprises an optical funnel.

14. A method for sorting cells comprising:
providing a single channel with only one output;
introducing a cell mix in a fluid into the channel;
optically sorting cells within the channel in a channel sorting region; and
killing or de-activating cells in a channel removal region downstream from the channel sorting region wherein the removal region extends only partially over the fluid flow path and wherein at least some cells do not flow into the removal region and flow to the channel output.

15. A method as claimed in claim 14 wherein the single channel has a single input and the cell mix is introduced via that input.

* * * * *